United States Patent
Zhu et al.

(10) Patent No.: US 8,993,772 B2
(45) Date of Patent: Mar. 31, 2015

(54) PROCESS FOR THE PREPARATION OF 4-AMINO-5-FLUORO-3-HALO-6-(SUBSTITUTED)PICOLINATES

(71) Applicant: Dow AgroSciences LLC, Indianapolis, IN (US)

(72) Inventors: Yuanming Zhu, Carmel, IN (US); Gregory T. Whiteker, Carmel, IN (US); James M. Renga, Indianapolis, IN (US); Kim E. Arndt, Carmel, IN (US); Gary Roth, Midland, MI (US); David E. Podhorez, Midland, MI (US); Scott P. West, Midland, MI (US); Yang Cheng, Midland, MI (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 14/222,912

(22) Filed: Mar. 24, 2014

(65) Prior Publication Data

US 2014/0206881 A1   Jul. 24, 2014

Related U.S. Application Data

(62) Division of application No. 13/356,686, filed on Jan. 24, 2012, now Pat. No. 8,754,231.

(60) Provisional application No. 61/435,936, filed on Jan. 25, 2011.

(51) Int. Cl.
  *C07D 213/803*  (2006.01)
  *C07D 213/81*   (2006.01)
  *C07D 213/78*   (2006.01)
  *C07D 213/79*   (2006.01)

(52) U.S. Cl.
  CPC ............ *C07D 213/81* (2013.01); *C07D 213/78* (2013.01); *C07D 213/79* (2013.01); *C07D 213/803* (2013.01)
  USPC ........................................................ 546/310

(58) Field of Classification Search
  None
  See application file for complete search history.

(56) References Cited

U.S. PATENT DOCUMENTS

| | | | |
|---|---|---|---|
| 3,285,925 A | 11/1966 | Johnston et al. | |
| 3,325,272 A | 6/1967 | Hamaker et al. | |
| 3,629,424 A | 12/1971 | Torba | |
| 3,803,159 A | 4/1974 | Torba | |
| 6,297,197 B1 | 10/2001 | Fields et al. | |
| 6,784,137 B2 | 8/2004 | Balko et al. | |
| 7,314,849 B2 | 1/2008 | Balko | |
| 7,432,227 B2 | 10/2008 | Balko | |
| 2009/0088322 A1 | 4/2009 | Epp et al. | |
| 2010/0041556 A1 | 2/2010 | Epp et al. | |

*Primary Examiner* — Zinna Northington Davis
(74) *Attorney, Agent, or Firm* — Michael R. Asam

(57) ABSTRACT

4-Amino-5-fluoro-3-halo-6-(substituted)picolinates are conveniently prepared from 4,5,6-trichloropicolinonitrile by a series of steps involving fluorine exchange, amination, halogen exchange, halogenation, nitrile hydrolysis, esterification, and transition metal assisted coupling.

4 Claims, No Drawings

PROCESS FOR THE PREPARATION OF 4-AMINO-5-FLUORO-3-HALO-6-(SUBSTITUTED)PICOLINATES

CROSS REFERENCE TO RELATED APPLICATIONS

This application is a divisional of U.S. application Ser. No. 13/356,686 filed Jan. 24, 2012, now U.S. Pat. No. 8,754,231 which claims the benefit of U.S. Provisional Patent Application Ser. No. 61/435,936 filed Jan. 25, 2011, the entireties of which are incorporated herein by reference.

FIELD OF THE INVENTION

The present invention concerns a process for the preparation of 4-amino-5-fluoro-3-halo-6-(substituted)picolinates. More particularly, the present invention concerns a process for the preparation of 4-amino-5-fluoro-3-halo-6-(substituted)picolinates in which the 5-fluoro substituent is introduced by a halogen exchange early in the process scheme.

BACKGROUND OF THE INVENTION

U.S. Pat. No. 6,297,197 B1 describes inter alia certain 4-amino-3-chloro-5-fluoro-6-(alkoxy or aryloxy)picolinate compounds and their use as herbicides. U.S. Pat. Nos. 6,784,137 B2 and 7,314,849 B2 describe inter alia certain 4-amino-3-chloro-5-fluoro-6-(aryl)picolinate compounds and their use as herbicides. U.S. Pat. No. 7,432,227 B2 describes inter alia certain 4-amino-3-chloro-5-fluoro-6-(alkyl)picolinate compounds and their use as herbicides. Each of these patents describes the manufacture of 4-amino-3-chloro-5-fluoropicolinate starting materials by fluorination of the corresponding 5-unsubstituted pyridines with 1-(chloromethyl)-4-fluoro-1,4-diazoniabicyclo[2.2.2]octane bis(tetrafluoroborate). It would be advantageous to produce 4-amino-5-fluoro-3-halo-6-(substituted)picolinates without having to rely on direct fluorination of the 5-position of the pyridine ring with an expensive fluorinating agent like 1-(chloromethyl)-4-fluoro-1,4-diazoniabicyclo[2.2.2]octane bis(tetrafluoroborate).

SUMMARY OF THE INVENTION

The present invention concerns a process for the preparation of 4-amino-5-fluoro-3-halo-6-(substituted)picolinates from 4,5,6-trichloropicolinonitrile. More particularly, the present invention concerns a process for the preparation of a 4-amino-5-fluoro-3-halo-6-(substituted)picolinate of the Formula I

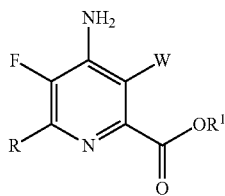

wherein
W represents Cl, Br or I;
R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and
$R^1$ represents $C_1$-$C_{12}$ alkyl or an unsubstituted or substituted $C_7$-$C_{11}$ arylalkyl; which comprises the following steps:

a) fluorinating 4,5,6-trichloropicolinonitrile (Formula A)

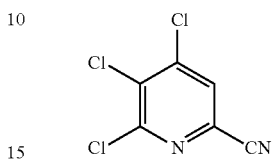

with a source of fluoride ion to produce 4,5,6-trifluoropicolinonitrile (Formula B)

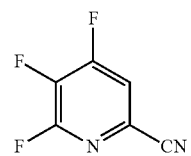

b) aminating 4,5,6-trifluoropicolinonitrile (Formula B) with ammonia to produce 4-amino-5,6-difluoropicolinonitrile (Formula C)

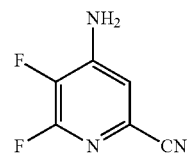

c) hydrolyzing the nitrile substituent and exchanging the fluoro substituent in the 6-position of 4-amino-5,6-difluoropicolinonitrile (Formula C) with an iodo, bromo or chloro substituent by treating with an iodide, bromide or chloride source to produce a 4-amino-5-fluoro-6-halopicolinamide of Formula D

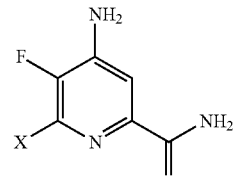

wherein X represents Cl, Br or I;

d) esterifying the 4-amino-5-fluoro-6-halopicolinamide of Formula D with an alcohol ($R^1$OH) and a Bronsted or Lewis acid to produce a 4-amino-5-fluoro-6-halopicolinate of Formula E

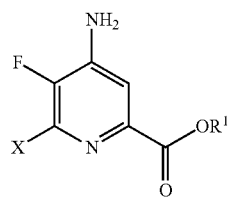

wherein $R^1$ represents $C_1$-$C_{12}$ alkyl or an unsubstituted or substituted $C_7$-$C_{11}$ arylalkyl;

e) halogenating the 4-amino-5-fluoro-6-halopicolinate of Formula E with a halogen source to produce a 4-amino-5-fluoro-3,6-dihalopicolinate of Formula F

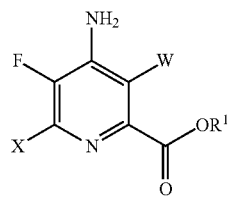

wherein W and X independently represent Cl, Br or I; and $R^1$ is as previously defined; and f) coupling the 4-amino-5-fluoro-3,6-dihalopicolinate of Formula F with an aryl, alkyl or alkenyl metal compound of the Formula G R-Met                                                         G wherein R is as previously defined and Met represents Zn-halide, Zn—R, tri-($C_1$-$C_4$ alkyl)tin, copper, or B(OR$^2$)(OR$^3$), where $R^2$ and $R^3$ are independent of one another, hydrogen, $C_1$-$C_4$ alkyl, or when taken together form an ethylene or propylene group in the presence of a transition metal catalyst to produce the 4-amino-3-halo-5-fluoro-6-(substituted)picolinate of Formula I.

The steps a) through f) may be performed in the order listed, as depicted in Scheme I.

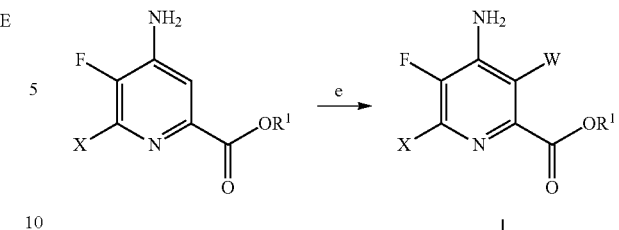

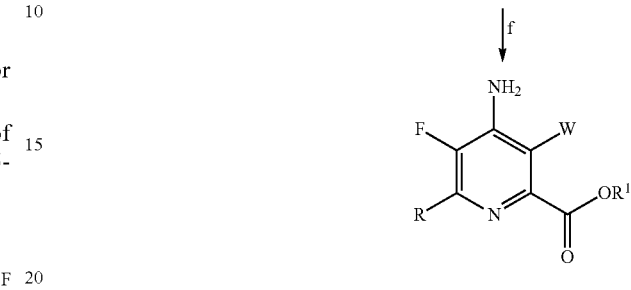

Alternatively, the order in which the steps are performed can be rearranged as illustrated, for example, in Schemes II, III and IV.

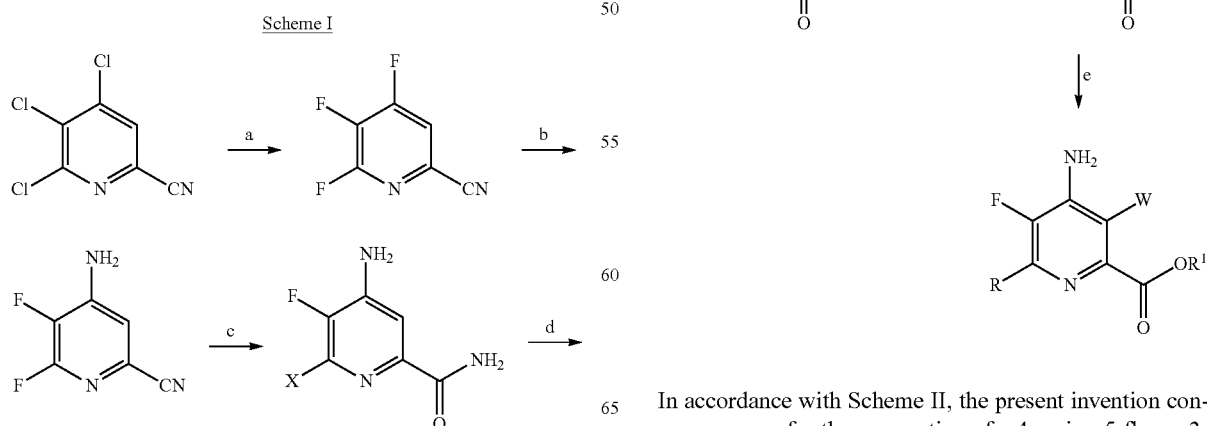

In accordance with Scheme II, the present invention concerns a process for the preparation of a 4-amino-5-fluoro-3-halo-6-(substituted)picolinate of the Formula I

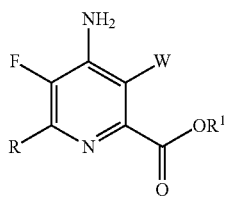

I wherein

W represents Cl, Br or I;

R represents $C_1$-$C_4$ alkyl, cyclopropyl, $C_2$-$C_4$ alkenyl, or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; which comprises the following steps:

a) fluorinating 4,5,6-trichloropicolinonitrile (Formula A)

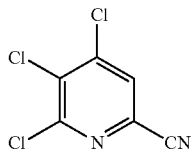

A with a source of fluoride ion to produce 4,5,6-trifluoropicolinonitrile (Formula B)

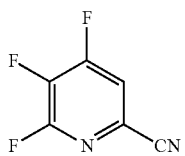

B b) aminating 4,5,6-trifluoropicolinonitrile (Formula B) with ammonia to produce 4-amino-5,6-difluoropicolinonitrile (Formula C)

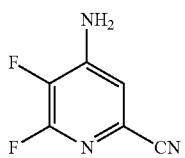

C c) hydrolyzing the nitrile substituent and exchanging the fluoro substituent in the 6-position of 4-amino-5,6-difluoropicolinonitrile (Formula C) with an iodo, bromo or chloro substituent by treating with an iodide, bromide or chloride source to produce a 4-amino-5-fluoro-6-halopicolinamide of Formula D

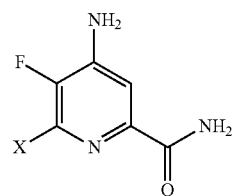

D wherein X represents Cl, Br or I;

d) esterifying the 4-amino-5-fluoro-6-halopicolinamide of Formula D with an alcohol ($R^1OH$) and a Bronsted or Lewis acid to produce a 4-amino-5-fluoro-6-halopicolinate of Formula E

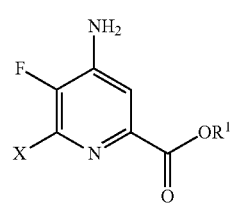

E wherein X represents Cl, Br or I; and $R^1$ represents $C_1$-$C_{12}$ alkyl or an unsubstituted or substituted $C_7$-$C_{11}$ arylalkyl;

e) coupling the 4-amino-5-fluoro-6-halopicolinate of Formula E with an aryl, alkyl or alkenyl metal compound of the Formula G R-Met      G wherein R is as previously defined and Met represents Zn-halide, Zn—R, tri-($C_1$-$C_4$ alkyl)tin, copper, or B($OR^2$)($OR^3$), where $R^2$ and $R^3$ are independent of one another, hydrogen, $C_1$-$C_4$ alkyl, or when taken together form an ethylene or propylene group in the presence of a transition metal catalyst to produce the 4-amino-5-fluoro-6-(substituted)-picolinate of Formula H

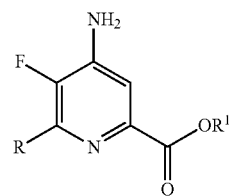

H wherein R and $R^1$ are as previously defined; and f) halogenating the 4-amino-5-fluoro-6-(substituted)picolinate of Formula H with a halogen source to produce a 4-amino-5-fluoro-3-halo-6-(substituted)picolinate of Formula I.

Scheme III

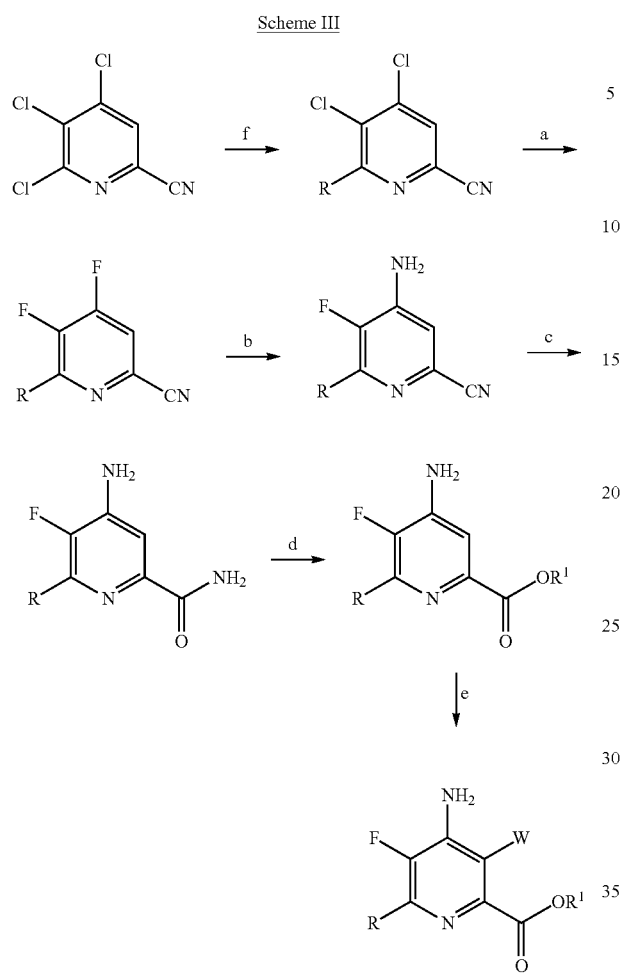

In Scheme III, the iodine, bromine or chlorine exchange portion of step c) is not necessary. Thus, the present invention also concerns a process for the preparation of a 4-amino-5-fluoro-3-halo-6-(substituted)picolinate of the Formula I

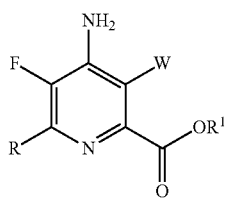

wherein

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; which comprises the following steps:

a) coupling 4,5,6-trichloropicolinonitrile (Formula A)

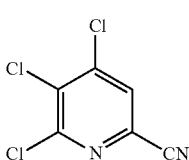

with an aryl, alkyl or alkenyl metal compound of the Formula G

R-Met            G wherein R is as previously defined and Met represents Zn-halide, Zn—R, tri-($C_1$-$C_4$ alkyl)tin, copper, or B($OR^2$)($OR^3$), where $R^2$ and $R^3$ are independent of one another, hydrogen, $C_1$-$C_4$ alkyl, or when taken together form an ethylene or propylene group in the presence of a transition metal catalyst to produce a 4,5-dichloro-6-(substituted)picolinonitrile of Formula J

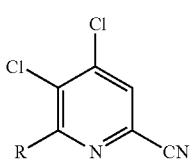

wherein R is as previously defined;

b) fluorinating the 4,5-dichloro-6-(substituted)picolinonitrile of Formula J with a fluoride ion source to produce a 4,5-difluoro-6-(substituted)picolinonitrile of Formula K

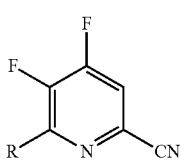

wherein R is as previously defined;

c) aminating the 4,5-difluoro-6-(substituted)picolinonitrile of Formula K with ammonia to produce a 4-amino-5-fluoro-6-(substituted)picolinonitrile of Formula L

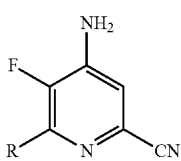

wherein R is as previously defined;

d) hydrolyzing the 4-amino-5-fluoro-6-(substituted)picolinonitrile of Formula L with an acid to produce the 4-amino-5-fluoro-6-(substituted)picolinamide of Formula M

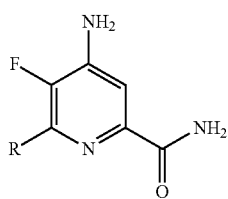

wherein R is as previously defined;

e) esterifying the 4-amino-5-fluoro-6-(substituted)picolinamide of Formula M with an alcohol ($R^1OH$) and a Bronsted or Lewis acid to produce the 4-amino-5-fluoro-6-(substituted)picolinate of Formula N

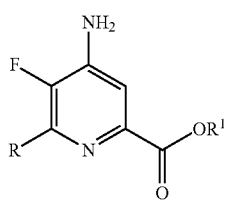

wherein R and $R^1$ are as previously defined; and f) halogenating the 4-amino-5-fluoro-6-(substituted)picolinate of Formula N with a halogen source to produce the 4-amino-5-fluoro-3-halo-6-(substituted)picolinate of Formula I.

Scheme IV

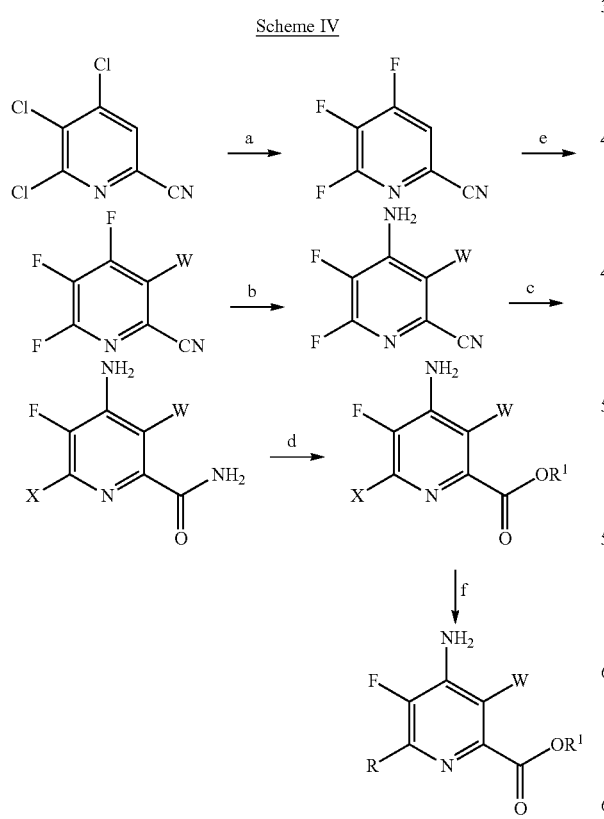

In accordance with Scheme IV, the present invention concerns a process for the preparation of a 4-amino-5-fluoro-3-halo-6-(substituted)picolinate of the Formula I

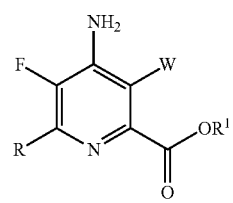

wherein

W represents Cl, Br or I;

R represents $C_1$-$C_4$ alkyl, cyclopropyl, $C_2$-$C_4$ alkenyl, or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; which comprises the following steps:

a) fluorinating 4,5,6-trichloropicolinonitrile (Formula A)

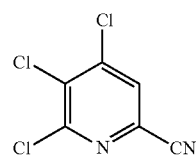

with a source of fluoride ion to produce 4,5,6-trifluoropicolinonitrile (Formula B)

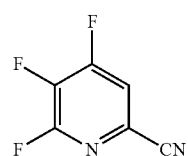

b) halogenating 4,5,6-trifluoropicolinonitrile (Formula B) with a halogen source to produce a 4,5,6-trifluoro-3-halopicolinonitrile of Formula O

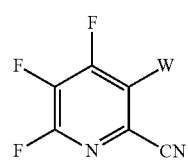

wherein

W represents Cl, Br or I;

c) aminating the 4,5,6-trifluoro-3-halopicolinonitrile of Formula O with ammonia to produce a 4-amino-5,6-difluoro-3-halo picolinonitrile of Formula P

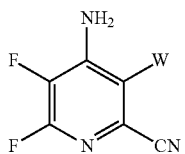

P wherein

W represents Cl, Br or I;

d) hydrolyzing the nitrile substituent and exchanging the fluoro substituent in the 6-position of the 4-amino-5,6-difluoro-3-halopicolinonitrile of Formula P with an iodo, bromo or chloro substituent by treating with an iodide, bromide or chloride source to produce a 4-amino-5-fluoro-3,6-dihalopicolinamide of Formula Q

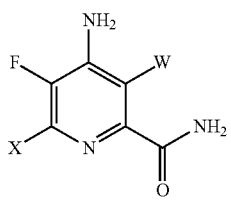

Q wherein W and X independently represent Cl, Br or I;

e) esterifying the 4-amino-5-fluoro-3,6-dihalopicolinamide of Formula Q with an alcohol ($R^1OH$) and a Bronsted or Lewis acid to produce a 4-amino-5-fluoro-3,6-dihalopicolinate of Formula F

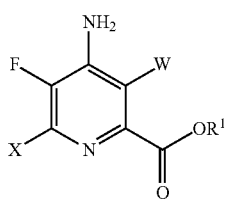

F wherein W and X independently represent Cl, Br or I; and $R^1$ represents $C_1$-$C_{12}$ alkyl or an unsubstituted or substituted $C_7$-$C_{11}$ arylalkyl; and f) coupling the 4-amino-5-fluoro-3,6-dihalopicolinate of Formula F with an aryl, alkyl or alkenyl metal compound of the Formula G R-Met  G wherein R is as previously defined and Met represents Zn-halide, Zn—R, tri-($C_1$-$C_4$ alkyl)tin, copper, or B($OR^2$)($OR^3$), where $R^2$ and $R^3$ are independent of one another, hydrogen, $C_1$-$C_4$ alkyl, or when taken together form an ethylene or propylene group in the presence of a transition metal catalyst to produce a 4-amino-5-fluoro-3-halo-6-(substituted)picolinate of Formula I.

Another aspect of the present invention is the novel intermediates produced during the present process, viz., compounds selected from the group consisting of:

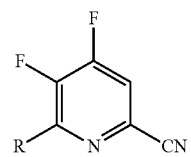

a)

wherein R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy;

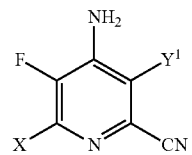

b)

wherein X represents I, Br, Cl or F, and $Y^1$ represents H, Cl, Br, or I;

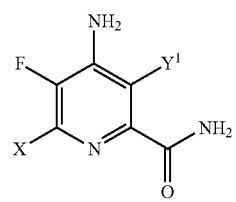

c)

wherein X represents I, Br, Cl or F, and $Y^1$ represents H, Cl, Br, or I;

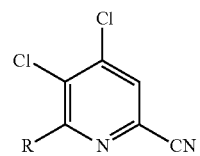

d)

wherein R represents $C_1$-$C_4$ alkyl, cyclopropyl, $C_2$-$C_4$ alkenyl, or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy;

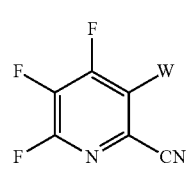

e)

wherein W represents Cl, Br or I; and

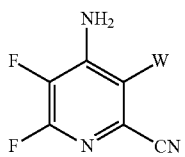

f)

wherein W represents Cl, Br or I.

DETAILED DESCRIPTION OF THE INVENTION

The terms "alkyl," "alkenyl" and "alkynyl," as well as derivative terms such as "alkoxy," "acyl," "alkylthio" and "alkylsulfonyl," as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "arylalkyl," as used herein, refers to a phenyl substituted alkyl group having a total of 7 to 11 carbon atoms, such as benzyl (—$CH_2C_6H_5$), 2-methylnaphthyl (—$CH_2C_{10}H_7$) and 1- or 2-phenethyl (—$CH_2CH_2C_6H_5$ or —$CH(CH_3)C_6H_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, C(O)O$C_1$-$C_6$alkyl, or where two adjacent substituents are taken together as —O($CH_2$)$_n$O— wherein n=1 or 2, provided that the substituents are sterically compatible and the rules of chemical bonding and strain energy are satisfied.

Unless specifically limited otherwise, the term "halogen," as well as derivative terms such as "halo," refers to fluorine, chlorine, bromine and iodine.

The phenyl groups substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy may be of any orientation, but 4-substituted phenyl, 2,4-disubstituted phenyl, 2,3,4-trisubstituted phenyl, 2,4,5-trisubstituted phenyl, and 2,3,4,6-tetrasubstituted phenyl isomers are preferred.

The 4-amino-5-fluoro-3-halo-6-(substituted)picolinates are prepared from 4,5,6-trichloropicolinonitrile by a series of steps involving fluorine exchange, amination, halogen exchange, halogenation, nitrile hydrolysis, esterification, and transition metal assisted coupling. The individual steps may be performed in different sequences.

The 4,5,6-trichloropicolinonitrile starting material is a known compound; see, for example, Example 15 in U.S. Pat. No. 6,784,137 B2.

In the fluorine exchange reaction, the fluorinated picolinonitrile is prepared by reacting the corresponding chlorinated picolinonitrile with at least one equivalent of fluoride ion source for each ring chlorine substituent to be exchanged.

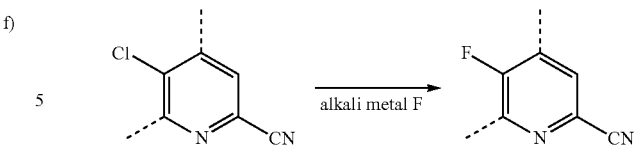

Typical fluoride ion sources are alkali metal fluorides which include sodium fluoride (NaF), potassium (KF) and cesium fluoride (CsF), with KF and CsF being preferred. Fluoride salts such as tetrabutylammonium fluoride (n-$Bu_4$NF) may also be used. Preferably, the reaction is carried out in a polar aprotic solvent or reaction medium such as dimethylsulfoxide (DMSO), N-methylpyrrolidinone (NMP), N,N-dimethylformamide (DMF), hexamethylphosphoramide (HMPA) or sulfolane. Additives such as crown ethers or phase-transfer agents which are known to increase the rate of fluoride exchange may also be used. The temperature at which the reaction is conducted is not critical but usually is from about 70° C. to about 180° C. and preferably from about 80° C. to about 120° C. Depending upon which solvent is employed in a particular reaction, the optimum temperature will vary. Generally speaking the lower the temperature the slower the reaction will proceed. The present reaction is typically conducted in the presence of vigorous agitation sufficient to maintain an essentially uniformly dispersed mixture of the reactants.

In conducting the fluorination reaction, neither the rate, nor the order, of addition of the reactants is critical. Usually, the solvent and alkali metal fluoride are mixed before the chlorinated picolinonitrile is added to the reaction mixture. A typical reaction generally requires from about 4 to about 100 hours and is usually conducted at ambient atmospheric pressure.

While the exact amount of reactants is not critical, it is preferred to employ an amount of alkali metal fluoride which will supply at least about an equimolar amount of fluorine atoms based on the number of chlorine atoms to be exchanged in the starting material, i.e., at least about an equimolar amount of alkali metal fluoride. After the reaction is completed the desired product is recovered by employing standard separation and purification techniques.

In the amination, a 4-fluoropicolinonitrile is reacted with ammonia to replace the fluorine atom with an amino group.

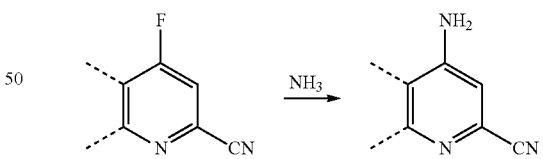

While only a stoichiometric amount of ammonia is required, it is often convenient to use a large excess of ammonia. The reaction is carried out in an inert solvent, preferably, a polar aprotic solvent or reaction medium such as DMSO, NMP, DMF, HMPA or sulfolane. Alternatively, aqueous ammonium hydroxide ($NH_4OH$) can be used, with or without use of an organic solvent. The temperature at which the reaction is conducted is not critical but usually is from about 0° C. to about 45° C. and preferably from about 10° C. to about 30° C.

In conducting the amination reaction, the 4-fluoropicolinonitrile is dissolved in the solvent, and the ammonia is added to the reaction mixture with cooling. Excess ammonia gas is typically bubbled into the reaction mixture. A typical reaction generally requires from about 0.5 to about 5 hours and is usually conducted at ambient atmospheric pressure.

In the halogen exchange and hydrolysis reaction, the 6-halopicolinamide is prepared by reacting the corresponding 6-fluoropicolinonitrile with at least two equivalents of a hydrogen halide (hydrogen iodide (HI), hydrogen bromide (HBr) or hydrogen chloride (HCl)).

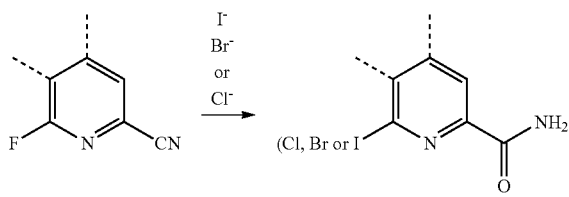

While only two equivalents of hydrogen halide are required, it is often convenient to use a large excess of the hydrogen halide. The reaction is carried out in an inert organic solvent, with $C_1$-$C_4$ alkanoic acids being especially preferred. The temperature at which the reaction is conducted is not critical but usually is from about 75° C. to about 150° C. and preferably from about 100° C. to about 130° C. The halogen exchange is conveniently conducted under pressure in a sealed vessel.

In conducting the halogenation and hydrolysis reactions, the 6-fluoropicolinonitrile can be heated with the hydrogen halide and alkanoic acid solvent in a sealed reactor. A typical reaction generally requires from about 0.5 to about 24 hours. The desired 6-halopicolinamide product is recovered by employing standard separation and purification techniques.

In the esterification reaction, the picolinamide is reacted with an alcohol in the presence of a Bronsted or Lewis acid.

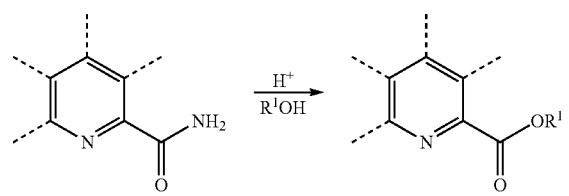

Strong protic Bronsted acids like sulfuric acid and phosphoric acid are typically employed in stoichiometric amounts. Lewis acids such like titanium(IV) isopropoxide may also be used. The reaction is carried out using the $C_1$-$C_{12}$ alkyl or an unsubstituted or substituted $C_7$-$C_{11}$ arylalkyl alcohol of the desired ester as solvent. The reaction is conveniently conducted in a sealed reactor generally above the boiling temperature of the alcohol solvent.

In conducting the esterification, the picolinamide or picolinonitrile is added to a mixture of the alcohol and acid. Although the temperature of reaction is not critical it is often heated to 80° C. to 140° C. for about 2 to about 24 hours, preferably to 100° C. to 120° C. for 6 to 8 hours The desired product is recovered by employing standard separation and purification techniques.

It is sometimes convenient to conduct the esterification step in conjunction with the workup of the halogen exchange step.

In the halogenation reaction, a chlorine, bromine or iodine atom is introduced into the 3-position of either the picolinate or picolinonitrile by reaction with a halogen source in an inert solvent.

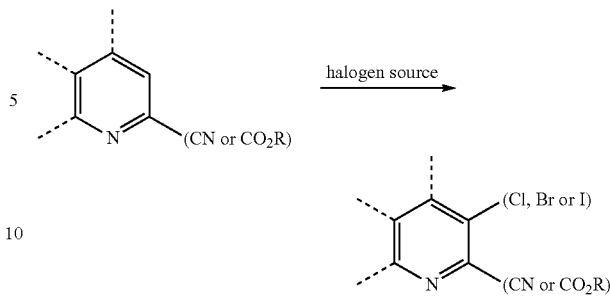

When the halogen atom at the 3-position is Cl, the chlorine source can be chlorine ($Cl_2$) itself or reagents such as sulfuryl chloride, N-chlorosuccinimide or 1,3-dichloro-5,5-dimethylhydantoin. When chlorine or sulfuryl chloride are used, a large excess of chlorinating agent is used. When chlorine gas is used, the reaction is performed in an inert solvent, preferably, a solvent such as dichloromethane, dichloromethane-water, carbon tetrachloride or acetic acid. When sulfuryl chloride is used, the reaction can be performed in an inert solvent, such as dichloromethane or in neat sulfuryl chloride. The temperature at which the reaction is conducted is not critical but usually is from about 0° C. to about 45° C. and preferably from about 10° C. to about 30° C. A typical reaction generally requires from about 0.5 to about 5 hours. The chlorination reaction is usually conducted at ambient atmospheric pressure. In some cases, chlorination does not occur under these conditions. Vapor-phase chlorination with a tubular reactor using chlorine gas can be used instead. The temperature at which the reaction is conducted is usually from about 350° C. to about 600° C. and preferably from about 500° C. to about 600° C. The chlorination reaction is usually conducted at ambient atmospheric pressure.

When the chlorinating agent used is N-chlorosuccinimide or 1,3-dichloro-5,5-dimethylhydantoin, the reaction is carried out using a stoichiometric amount of chlorinating reagent. For chlorinations using 1,3-dichloro-5,5-dimethylhydantoin as the chlorinating agent, both chlorines in the hydantoin are found to react. The reaction is performed in an inert polar solvent, such as DMF or acetonitrile. The temperature at which the reaction is conducted is not critical but usually is from about 20° C. to about 85° C. and preferably from about 50° C. to about 80° C. When acetonitrile is used as solvent, it is convenient to carry out the reaction at the reflux temperature. A typical reaction generally requires from about 0.5 to about 5 hours. The chlorination reaction is usually conducted at ambient atmospheric pressure.

When the halogen atom at the 3-position is Br, the bromine source can be bromine ($Br_2$) itself or reagents such as sulfuryl bromide, N-bromosuccinimide or 1,3-dibromo-5,5-dimethylhydantoin. When $Br_2$ is used as brominating agent, a large excess can be employed, and the reaction is performed in an inert solvent, preferably, a solvent such as dichloromethane, dichloromethane-water or acetic acid. The temperature at which the reaction is conducted is not critical but usually is from about 0° C. to about 45° C. and preferably from about 10° C. to about 30° C. A typical reaction generally requires from about 0.5 to about 5 hours. The bromination reaction is usually conducted at ambient atmospheric pressure.

When the brominating agent used is N-bromosuccinimide or 1,3-dibromo-5,5-dimethylhydantoin, the reaction is carried out using a stoichiometric amount of brominating reagent. The reaction is performed in an inert polar solvent, such as DMF or acetonitrile. The temperature at which the reaction is conducted is not critical but usually is from about 20° C. to about 85° C. and preferably from about 50° C. to about 80° C. When acetonitrile is used as solvent, it is convenient to carry out the reaction at the reflux temperature. A typical reaction generally requires from about 0.5 to about 5 hours. The bromination reaction is usually conducted at ambient atmospheric pressure.

When the halogen atom at the 3-position is I, the iodine source can be iodine ($I_2$) itself or reagents such as iodine monochloride or N-iodosuccinimide Periodic acid may be used in conjunction with $I_2$. When $I_2$ is used as iodinating agent, a large excess can be employed, and the reaction is performed in an inert solvent, preferably, a solvent such as dichloromethane, dichloromethane-water or acetic acid. The temperature at which the reaction is conducted is not critical but usually is from about 0° C. to about 45° C. and preferably from about 10° C. to about 30° C. A typical reaction generally requires from about 0.5 to about 5 hours. The iodination reaction is usually conducted at ambient atmospheric pressure.

In the coupling reaction, a 6-iodo-, bromo- or chloropicolinate or picolinonitrile is allowed to react with an aryl, alkyl or alkenyl metal compound where the metal is a Zn-halide, Zn—R, tri-($C_1$-$C_4$ alkyl)tin, copper, or B($OR^2$)($OR^3$), where $R^2$ and $R^3$ are independent of one another, hydrogen, $C_1$-$C_4$ alkyl, or when taken together form an ethylene or propylene group, in the presence of a transition metal catalyst.

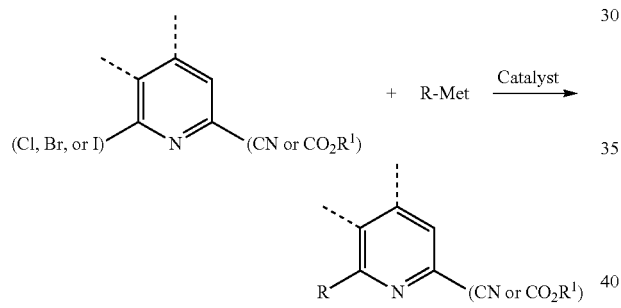

"Catalyst" is a transition metal catalyst, in particular a palladium catalyst such as palladium(II) acetate or bis(triphenylphosphine)palladium(II) dichloride, or a nickel catalyst such as nickel(II) acetylacetonate or bis(triphenylphosphine)nickel(II) dichloride. In addition, catalysts can be prepared in situ from metal salts and ligands, such as palladium(II) acetate and triphenylphosphine or nickel(II) chloride and triphenylphosphine. These in situ catalysts can be prepared by prior reaction of metal salt and ligand, followed by addition to the reaction mixture, or by separate addition of the metal salt and ligand directly to the reaction mixture.

Typically, coupling reactions are carried out in the absence of oxygen using an inert gas, such as nitrogen or argon. Techniques used to exclude oxygen from coupling reaction mixtures, such as sparging with inert gas, are well known to those skilled in the art. Examples of such techniques are described in *The Manipulation of Air-Sensitive Compounds*, 2nd ed., D. F. Shriver, M. A. Drezdzon, Eds.; Wiley-Interscience, 1986. Sub-stoichiometric amounts of a catalyst are used, typically from about 0.0001 equivalents to 0.1 equivalents. Additional amounts of ligand may optionally be added to increase catalyst stability and activity. In addition, additives such as sodium carbonate ($Na_2CO_3$), potassium carbonate ($K_2CO_3$), KF, CsF and NaF are typically added to the coupling reaction. The coupling reaction generally requires from about 1 to about 5 equivalents of such additive, preferably from 1 to 2 equivalents. Water may optionally be added to the coupling reaction to increase the solubility of these additives. The coupling reaction generally requires from 1 to about 3 equivalents of an aryl, alkyl or alkenyl metal compound, preferably from 1 to 1.5 equivalents. The reaction is carried out in an inert solvent, such as toluene, tetrahydrofuran (THF), dioxane or acetonitrile. The temperature at which the reaction is conducted is not critical but usually is from about 25° C. to about 150° C. and preferably from about 50° C. to about 125° C. A typical reaction generally requires from about 0.5 to about 24 hours. No particular order of addition of reactants is typically required. It is often operationally simpler to combine all reactants except the catalyst and then deoxygenate the reaction solution. Following deoxygenation, the catalyst can be added to commence the coupling reaction.

When the Met portion of the aryl, alkyl or alkenyl metal compound is a Zn-halide, Zn—R or copper, protection of reactive functional groups may be necessary. For example, if an amino substituent (—NHR or —$NH_2$) is present, protection of these reactive groups may be required. A variety of groups are known in the art for protection of amino groups from reaction with organometallic reagents. Examples of such protecting groups are described in *Protective Groups in Organic Synthesis*, $3^{rd}$ ed.; Greene, T. W.; Wuts, P. G. M, Eds.; Wiley-Interscience, 1999. The choice of which metal to use in R-Met is influenced by a number of factors, such as cost, stability, reactivity and the need to protect reactive functional groups.

The products obtained by any of these processes, can be recovered by conventional means, such as evaporation or extraction, and can be purified by standard procedures, such as by recrystallization or chromatography.

The following examples are presented to illustrate the invention.

EXAMPLES

Fluorine Exchange

Example 1a 4,5,6-Trifluoropicolinonitrile

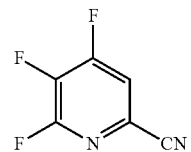

A 100 milliliter (mL) three-neck flask equipped with a mechanical stirrer, a thermocouple, and a vacuum distillation head was charged with anhydrous DMSO (50 mL) and CsF (8.71 grams (g), 57.4 millimoles (mmol)) under nitrogen. The apparatus was evacuated and heated to 60° C. with stiffing to enable the drying of the system by distilling off DMSO (15 mL) and trace amounts of water. 4,5,6-Trichloropicolinonitrile (3.4 g, 16.3 mmol) was added. The reaction mixture was heated at 75° C. (20.5 hours (h)) and then at 110° C. (2.5 h). Additional CsF (2.23 g) was added, and heating at 110° C. was continued for an additional hour. Upon cooling, the reaction mixture was poured into cold saturated (satd) aqueous (aq) sodium bicarbonate ($NaHCO_3$) solution under stiffing and was extracted with ether ($Et_2O$). The combined organic extracts were washed with brine, dried over sodium sulfate (Na$_2$SO$_4$), filtered and concentrated under vacuum to give a brown oil (2.51 g): EIMS m/z 158.

Example 1b 4,5,6-Trifluoropicolinonitrile

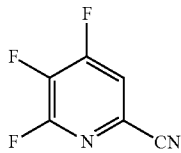

To a 45 mL stainless steel pressure vessel was added 4,5,6-trichloropicolinonitrile (1.0 g, 4.8 mmol), dry KF (1.3 g 22.4 mmol), 18-crown-6 (180 mg, 0.7 mmol) and dry acetonitrile (10 mL). The vessel was sealed and heated at 135° C. for 10 h. After cooling, the vessel was sampled at which time analysis by gas chromatography (GC) indicated the mixture contained 70% 4,5,6-trifluoropicolinonitrile and 30% 5-chloro-4,6-difluoropicolinonitrile: EIMS (70 eV) m/z 158 (M$^+$, 100%), 131 (20%), 176 (M$^+$, 30%), 174 (M$^+$, 100%).

Example 1c 6-(4-Chlorophenyl)-4,5-difluoropicolinonitrile

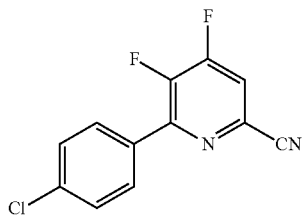 [SMILES: N#Cc1cc(F)c(F)c(-c2ccc(Cl)cc2)n1]

A 1000 mL three-neck flask was equipped with a distillation head, nitrogen inlet, mechanical stirrer and thermocouple. The flask was loaded with CsF (93.6 g, 0.616 mol). Anhydrous DMSO (500 mL) was added, and the suspension was evacuated/backfilled with nitrogen. The suspension was heated to 80° C. for 30 min. DMSO (100 mL) was distilled off under vacuum to remove residual water. 4,5-Dichloro-6-(4-chlorophenyl)picolinonitrile (50 g, 0.1763 mol) was added, and the solution was evacuated/backfilled with nitrogen. The reaction mixture was heated to 105° C. under nitrogen. After 4 h at 105° C., GC analysis showed completion of reaction. The reaction mixture was allowed to cool to room temperature. DMSO was removed by vacuum distillation. The residue was poured into ice water (500 g) and extracted with ethyl acetate (EtOAc; 3×200 mL). The combined organic extracts were washed with water (2×200 mL) and then brine (100 mL). The extracts were dried over anhydrous Na$_2$SO$_4$, filtered and concentrated under vacuum to give a brown oil which crystallized upon standing. Purification by column chromatography ((60-120 mesh silica; eluting with 0-20% EtOAc-hexane gradient) gave a white solid (17 g, 39%): mp 89.0-90.8° C.; $^1$H NMR (400 MHz, DMSO-d$_6$) δ 8.51-8.47 (m, 1H), 7.92 (d, J$_{H-H}$=8.6 Hz, 2H), 7.64 (d, J$_{H-H}$=8.6 Hz, 2H); $^{13}$C NMR (100 MHz, DMSO-d$_6$) δ 156.04 (dd, J$_{F-C}$=262, 13 Hz), 148.16 (dd, J$_{F-C}$=9, 2 Hz), 147.99 (dd, J$_{F-C}$=267, 10 Hz), 135.72, 131.17 (dd, J$_{F-C}$=15, 3 Hz), 130.4 (d, J$_{F-C}$=6 Hz), 129.08 (dd, J$_{F-C}$=11, 7 Hz), 128.91, 118.93 (d, J$_{F-C}$=19 Hz), 115.96 (d, J$_{F-C}$=3 Hz); $^{19}$F NMR (376.5 MHz, DMSO-d$_6$) δ −123.25 (d, J$_{F-F}$=18.82 Hz), −141.07 (d, J$_{F-F}$=18.82 Hz); ESIMS m/z 251 ([M]$^+$). Anal. Calcd. for C$_{12}$H$_5$ClF$_2$N$_2$: C, 57.51; H, 2.01; N, 11.18. Found: C, 57.97; H, 2.15; N, 10.77.

Amination

Example 2a

4-Amino-5,6-difluoropicolinonitrile

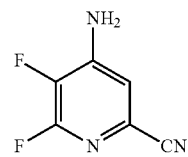

Ammonium hydroxide (NH$_4$OH) was added to crude 4,5,6-trifluoropicolinonitrile (2.5 g, 15.8 mmol) and stirred at room temperature for 2 h. A brown solid formed which was filtered, washed with water and dried to give 0.72 g. Analysis by gas chromatography-mass spectroscopy (GC-MS) indicated the presence of two isomeric products. The aqueous filtrate was extracted with EtOAc. The combined organic extracts were washed with brine, dried over Na$_2$SO$_4$, and evaporated to give additional brown solid. The two crops were combined and purified by silica gel chromatography to give 4-amino-5,6-difluoro-picolinonitrile (0.60 g, 24.4%): $^1$H NMR (400 MHz, CDCl$_3$) δ 7.13 (d, J=5.3 Hz, 1H, aromatic), 6.62 (s, 2H, NH$_2$); $^{13}$C NMR (101 MHz, CDCl$_3$) δ 157.0 (dd, J=235, 12 Hz), 151.7 (dd, J=10, 7 Hz), 139.5 (dd, J=254, 29 Hz), 128.8 (d, J=19 Hz), 121.2 (s), 121.0 (s); $^{19}$F NMR (376 MHz, CDCl$_3$) δ −85.29 (d, J=24.5 Hz), −156.98 (dd, J=24.5, 5.2 Hz).

Example 2b

4-Amino-3-chloro-5,6-difluoropicolinonitrile

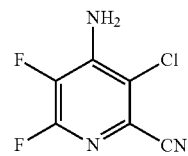

A solution of 3-chloro-4,5,6-trifluoropicolinonitrile (200 g) in EtOAc (3 L) was cooled to 10° C. To this was slowly added 14% aq NH$_4$OH (1296 g) keeping the temperature between 18-23° C. The aqueous solution was separated from the organic solution. The organic phase was washed sequentially with a 50/50 solution of aqueous saturated NaCl and water (500 mL) and satd NaCl solution (250 mL). The organic phase was concentrated under vacuum at 50° C. to about 500 mL volume as the product crystallized out. To this slurry was added heptane (1 L), and the mixture was concentrated under vacuum. The solids were collected by filtration. This solid was washed with pentane and dried under vacuum to give 4-amino-3-chloro-5,6-difluoropicolinonitrile (173.8 g, 90%, 99.6% purity) as a white crystalline solid: mp 190-191.5° C.; $^{13}$CNMR (101 MHz, DMSO-d$_6$) δ 150.03 (dd, J=232.4, 12.5 Hz, C6), 144.29 (dd, J=11.4, 6.9 Hz, C4), 133.72 (dd, J=257.9, 30.8 Hz, C5), 122.14 (dd, J=19.6, 4.9 Hz, C2), 119.31 (s, C3), 114.25 (s, CN); $^{19}$F NMR (376 MHz, DMSO-d$_6$) δ −91.24 (d, J=24.2 Hz), −154.97 (d, J=24.2 Hz); ELMS m/z 189 (Mr). Anal. Calcd for C$_6$H$_2$ClF$_2$N$_3$: C, 38.02; H, 1.06; N, 22.17. Found: C. 37.91; H. 1.00; 22.02.

Example 2c

4-Amino-6-(4-chlorophenyl)-5-fluoropicolinonitrile

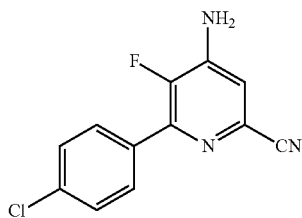 [SMILES: N#Cc1cc(N)c(F)c(-c2ccc(Cl)cc2)n1]

6-(4-Chlorophenyl)-4,5-difluoropicolinonitrile (60 g, 0.24 mol) was dissolved in DMSO (1200 mL). Ammonia was periodically bubbled through the solution for a total of 24 h over a period of 48 h. The reaction mixture was poured into ice water (2000 g). The product was extracted with EtOAc (3×500 mL). The combined organic layers were washed with water (5×500 mL) and then brine (100 mL). The extracts were dried over anhydrous Na$_2$SO$_4$, filtered and concentrated under vacuum to give a white solid (50 g, 84%): mp 185.3-187.8° C.; $^1$H NMR (400 MHz, DMSO-d$_6$) δ 7.85 (d, J$_{H-H}$=8.5 Hz, 2H), 7.58 (d, J$_{H-H}$=8.5 Hz, 2H), 7.21 (d, J$_{F-H}$=6.0 Hz, 1H), 6.96 (br s, 2H); $^{13}$C NMR (100 MHz, DMSO-d$_6$) δ 141.86 (d, J$_{F-C}$=256 Hz), 144.81 (d, J$_{F-C}$=14 Hz), 143.80 (d, J$_{F-C}$=10 Hz), 134.34, 132.87 (d, J$_{F-C}$=5 Hz), 130.3 (d, J$_{F-C}$=6 Hz), 128.56, 128.38 (d, J$_{F-C}$=5 Hz), 117.43, 115.08 (d, J$_{F-C}$=5 Hz); $^{19}$F NMR (376.5 MHz, DMSO-d$_6$) δ −142.71; ESIMS m/z 248 ([M]$^+$). Anal. Calcd. for C$_{12}$H$_7$ClFN$_3$: C, 58.20; H, 2.85; N, 16.97. Found: C, 57.82; H, 3.022; N, 16.10.

Halogen Exchange, Hydrolysis and Esterification

Example 3a

Methyl 4-amino-6-bromo-5-fluoropicolinate

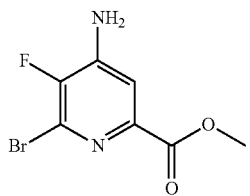

4-Amino-5,6-difluoropicolinonitrile (4.5 g, 6.45 mmol) was dissolved in 30% HBr in acetic acid (40 mL). The solution was heated to 120° C. in a Parr reaction vessel for 3.0 h. Upon cooling, the solution was concentrated under vacuum. The residue was dissolved in methyl alcohol (CH$_3$OH; 40 mL) and transferred back to the Parr reactor. Concentrated sulfuric acid was added (632 mg, 6.45 mmol), and the reactor was heated at 110° C. for 7 h. Upon cooling, the solvent was evaporated under vacuum. The residue was dissolved in EtOAc and neutralized with satd aq NaHCO$_3$ solution. The organic phase was separated, washed with brine, dried (Na$_2$SO$_4$) and evaporated. The crude product was purified by silica gel chromatography (10-100% EtOAc in hexane) to give a yellow solid (2.87 g, 40%): mp 187-190° C.; $^1$H NMR (400 MHz, DMSO-d$_6$) δ 7.46 (d, J=6.2 Hz, 1H, aromatic), 6.88 (s, 2H, NH$_2$), 3.83 (s, 3H, CH$_3$); $^{13}$C NMR (101 MHz, DMSO-d$_6$) δ 163.8 (s), 144.7 (d, J=252 Hz), 144.3 (d, J=13 Hz), 143.1 (d, J=5 Hz), 127.7 (d, J=21 Hz), 113.1 (d, J=5 Hz), 52.4 (s); $^{19}$F NMR (376 MHz, DMSO-d$_6$) δ −133.77 (s).

Example 3b

4-Amino-6-bromo-3-chloro-5-fluoropicolinamide and methyl 4-amino-6-bromo-3-chloro-5-fluoropicolinate

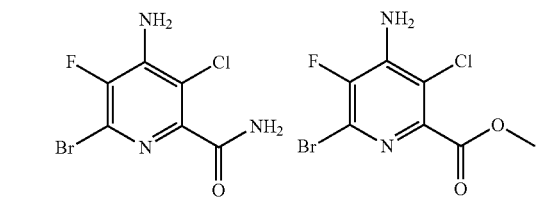

A mixture of 4-amino-3-chloro-5,6-difluoropicolinonitrile (70 g, 0.37 mol) and 33% HBr in acetic acid (700 mL) was heated to 120° C. in a sealed, stirred reaction vessel for 2 h. After cooling to room temperature, the supernatant was separated from a large amount of a tan solid and concentrated under vacuum to give a tacky dark residue. This residue was taken into CH$_3$OH (600 mL) and added back to the tan solids that remained in the pressure reactor. To this mixture was slowly added concentrated sulfuric acid (H$_2$SO$_4$; 40 g, 0.41 mol), and the reactor was again sealed and heated to 110° C. for 6 h. The cooled reaction mixture was slowly poured into satd aq sodium carbonate (Na$_2$CO$_3$; 2 L) and Et$_2$O (1 L). The ether extract was dried over MgSO$_4$, filtered and concentrated to a tan solid. This solid was purified by column chromatography to give methyl 4-amino-6-bromo-3-chloro-5-fluoropicolinate (78 g, 75%) as fine white crystals: mp 119-120° C.; $^1$H NMR (400 MHz, DMSO-d$_6$) δ 7.28 (s, 2H), 3.87 (s, 3H); $^{13}$C NMR (101 MHz, DMSO-d$_6$) δ 163.54 (s, C=O), 144.63 (d, J=256.3 Hz, C5), 142.60 (d, J=4.9 Hz, C2), 140.55 (d, J=13.6 Hz, C4), 125.61 (d, J=21.0 Hz, C6), 116.65 (s, C3), 53.2 (s, OMe); $^{19}$F NMR (376 MHz, CDCl$_3$) δ −128.86; EIMS m/z 284 (Mr). Anal. Calcd for C$_7$H$_5$BrClFN$_2$O$_2$: C, 29.66; H, 1.78; N, 9.88. Found: C, 30.03; H, 1.80; N, 9.91.

Also isolated by column chromatography was 4-amino-6-bromo-3-chloro-5-fluoropicolinamide (200 mg) as a light tan solid: mp. 215° C. dec; $^{13}$CNMR (101 MHz, DMSO-d$_6$) δ 165.64 (s, C=O), 148.02 (d, J=4.8 Hz, C2), 142.31 (d, J=233.2 Hz, C5), 141.86 (d, J=14.0 Hz, C4), 124.13 (d, J=19.9 Hz, C6), 112.55 (d, J=2.1 Hz, C3); $^{19}$F NMR (376 MHz, DMSO-d$_6$) δ −131.56; EIMS m/z 269 ([M]$^+$). Anal. Calcd for C$_6$H$_4$BrClFN$_3$O: C, 26.84; H, 1.50; N, 15.65. Found: C, 26.95; H, 1.52; N, 15.16.

Hydrolysis and Esterification

Example 4a

Methyl 4-amino-6-(4-chlorophenyl)-5-fluoropicolinate

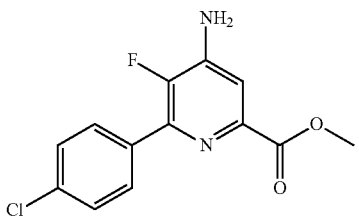 [SMILES: COC(=O)c1cc(N)c(F)c(-c2ccc(Cl)cc2)n1]

A 1000 mL sealed tube was loaded with 4-amino-6-(4-chlorophenyl)-5-fluoropicolinonitrile (30 g, 0.1211 mol) and 90% H$_2$SO$_4$ (30 mL) in CH$_3$OH (500 mL). The solution was heated at 110° C. for 7 days. A white solid precipitated upon cooling to room temperature. The reaction mixture was poured into ice water (300 g), neutralized with satd NaHCO$_3$ solution and then extracted with EtOAc (3×200 mL). The combined organic extracts were washed with water (3×100 mL) and then brine. The extracts were dried over anhydrous Na$_2$SO$_4$, filtered and concentrated under vacuum to give a white solid. Purification by column chromatography (60-120 mesh silica; eluting with 0-20% EtOAc-hexane gradient) gave a white solid (25 g, 44%): mp 176.8-178.9° C.; $^1$H NMR (400 MHz, DMSO-d$_6$) δ 7.87 (d, J$_{H-H}$=8.6 Hz, 2H), 7.56 (d, 8.6 Hz, 2H), 7.46 (d, J$_{H-F}$=6.3 Hz, 1H), 6.64 (br s, 2H), 3.38 (s, 3H); $^{13}$C NMR (100 MHz, DMSO-d$_6$) δ 165.44, 147.69 (d, J$_{F-C}$=254 Hz), 144.82 (d, J$_{F-C}$=13 Hz), 143.72 (d, J$_{F-C}$=5 Hz), 142.56 (d, J$_{F-C}$=11 Hz), 133.34 (d, J$_{F-C}$=7 Hz), 130.75 (d, J$_{F-C}$=6 Hz), 128.88, 112.44 (d, J$_{F-C}$=5 Hz), 52.73; $^{19}$F NMR (376.5 MHz, DMSO-d$_6$) δ −145.01; ESIMS m/z 281 ([M]$^+$). Anal. Calcd. for C$_{13}$H$_{10}$ClFN$_2$O$_2$: C, 55.63; H, 3.59; N, 9.98. Found: C, 55.59; H, 3.61; N, 9.98.

Coupling

Example 5a

Methyl 4-amino-5-fluoro-6-(4-chloro-2-fluoro-3-methoxyphenyl)-picolinate

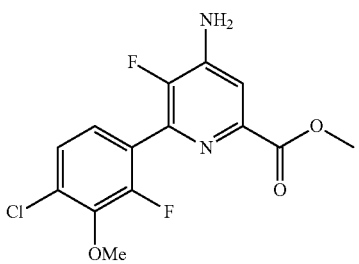 [SMILES: COC(=O)c1cc(N)c(F)c(-c2ccc(Cl)c(OC)c2F)n1]

A 50 mL round bottom flask equipped with a reflux condenser was charged with solid methyl 4-amino-6-bromo-5-fluoropicolinate (1.0 g, 4.02 mmol), 2-(4-chloro-2-fluoro-3-methoxyphenyl)-1,3,2-dioxaborinane (1.227 g, 5.02 mmol), bis(triphenylphosphine)-palladium(II) dichloride (Pd(PPh$_3$)$_2$Cl$_2$; 0.141 g, 0.201 mmol), and KF (0.467 g, 8.03 mmol). The reaction mixture was flushed with nitrogen, and then solvent (3:1 acetonitrile-water, 24 mL) was added. The reaction mixture was heated to reflux under nitrogen for 2 h. Upon cooling to room temperature, the product was filtered, washed with acetonitrile followed by water, and dried in a vacuum oven overnight to give the product (0.89 g) as an off-white solid: mp 204-206° C. An additional 0.29 g of product was isolated from the filtrate for a combined yield of 89%. $^1$H NMR (400 MHz, DMSO-d$_6$) δ 7.54 (d, J=6.6 Hz, 1H), 7.46 (dd, J=8.5, 1.4 Hz, 1H), 7.30 (dd, J=8.4, 7.2 Hz, 1H), 6.71 (s, 2H), 3.93 (s, 3H), 3.83 (s, 3H), 3.31 (s, 4H); $^{13}$C NMR (101 MHz, DMSO-d$_6$) δ 164.82 (s), 153.17 (d, J=249.5 Hz), 146.87 (d, J=254.3 Hz), 143.83 (dd, J=13.4, 3.8 Hz), 143.69 (d, J=4.3 Hz), 139.05 (d, J=10.6 Hz), 128.20 (d, J=3.2 Hz), 125.96 (d, J=3.4 Hz), 125.42 (d, J=3.6 Hz), 123.83 (dd, J=14.3, 3.1 Hz), 112.54 (s), 61.56 (s), 52.25 (s); $^{19}$F NMR (376 MHz, DMSO-d$_6$) δ −129.37 (d, J=26.0 Hz), −142.56 (d, J=26.3 Hz).

Example 5b

Methyl 4-amino-3-chloro-5-fluoro-6-(4-chloro-2-fluoro-3-methoxy-phenyl)picolinate

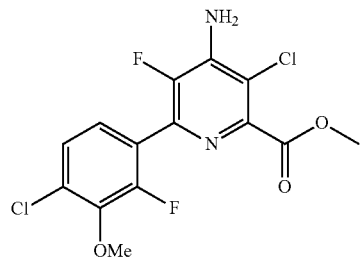 [SMILES: COC(=O)c1nc(-c2ccc(Cl)c(OC)c2F)c(F)c(N)c1Cl]

A 250 mL three-neck flask equipped with a reflux condenser, a nitrogen inlet and a thermocouple was charged with methyl 4-amino-3,6-dichloro-5-fluoropicolinate (9.965 g, 41.7 mmol), 2-(4-chloro-2-fluoro-3-methoxyphenyl)-1,3,2-dioxaborinane (12.74 g, 52.1 mmol) and KF (4.84 g, 83 mmol). Acetonitrile (78 mL) and water (26 mL) were added. The reaction mixture was purged with nitrogen. Pd(PPh$_3$)$_2$Cl$_2$ (1.477 g, 2.10 mmol, 5 mol %) was added, and the solution was heated to 70° C. under nitrogen for 2 h. Upon cooling to room temperature, a precipitate formed which was filtered and washed with water. The precipitate was dissolved in EtOAc (ca 500 mL) and washed with water and then brine. The organic layer was dried (MgSO$_4$) and the solvent was removed using a rotary evaporator to give an orange solid, which was dried in a vacuum oven at 50° C. (11.46 g, 76% yield): mp 169-170.5° C.; $^1$H NMR (400 MHz, DMSO-d$_6$) δ 7.48 (d, J=8.4 Hz, 1H), 7.32 (t, J=7.7 Hz, 1H), 7.15 (s, 2H), 3.96 (s, 3H), 3.90 (s, 3H); $^{13}$C NMR (101 MHz, DMSO-d$_6$) δ 164.85 (s), 153.11 (d, J=252.5 Hz), 146.29 (s), 144.52 (d, J=4.3 Hz), 143.74 (s), 142.75 (dd, J=227.1, 14.0 Hz), 136.38 (d, J=13.4 Hz), 128.58 (d, J=3.2 Hz), 125.87 (s), 125.54 (d, J=3.5 Hz), 122.89 (dd, J=13.8, 4.0 Hz), 113.01 (d, J=3.0 Hz), 61.61 (d, J=4.2 Hz), 52.70 (s); ESIMS m/z 364 ([M+H]$^+$). Anal. Calcd for C$_{14}$H$_{10}$Cl$_2$F$_2$N$_2$O$_3$: C, 46.30; H, 2.78; N, 7.71. Found: C, 46.60; H, 2.68; N, 7.51.

Example 5c

4-Amino-3-chloro-5-fluoro-6-(4-chloro-2-fluoro-3-methoxy-phenyl)picolinonitrile

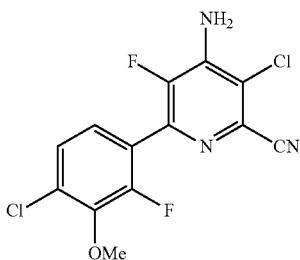 [SMILES: COc1c(Cl)ccc(-c2nc(C#N)c(Cl)c(N)c2F)c1F]

A mixture of 4-amino-3,6-dichloro-5-fluoropicolinonitrile (0.37 g, 1.80 mmol), 2-(4-chloro-2-fluoro-3-methoxyphenyl)-1,3,2-dioxaborinane (0.549 g, 2.24 mmol) and KF (0.209 g, 3.59 mmol) was taken into acetonitrile (6.75 mL) and water (2.25 mL). The mixture was stirred and sparged with a nitrogen atmosphere. Pd(PPh$_3$)$_2$Cl$_2$ (63 mg, 0.1 mmol) was added, and the mixture was again sparged with nitrogen. The solution was then heated to 75° C. under nitrogen for 2 h. Upon cooling down, a precipitate formed and was collected by filtration, washed with water and dried under vacuum to give the product (0.34 g) as an off-white solid. The aqueous phase was extracted with EtOAc (3×), and the combined organic extracts were washed with brine, dried, and concentrated. Purification by silica gel chromatography gave additional product (0.12 g) as a white solid. Total yield 78%. $^1$H NMR (400 MHz, DMSO-d$_6$) δ 7.50 (dd, J=8.5, 1.4 Hz, 1H), 7.45 (s, 2H), 7.33 (dd, J=8.5, 7.2 Hz, 1H), 3.94 (s, 3H); $^{13}$C NMR (101 MHz, DMSO-d$_6$) δ 152.97 (d, J=253.2 Hz), 145.73 (d, J=260.8 Hz), 143.82 (d, J=13.7 Hz), 141.83 (d, J=14.7 Hz), 138.45 (d, J=14.8 Hz), 133.93-132.79 (m), 128.93 (d, J=3.3 Hz), 127.74 (s), 126.37-125.10 (m), 122.08 (dd, J=13.6, 3.9 Hz), 119.34 (d, J=4.5 Hz), 114.99 (s), 61.61 (s); $^{19}$F NMR (376 MHz, DMSO-d$_6$) δ −129.00 (dd, J=28.2, 7.0 Hz, 1F), −133.76 (d, J=28.2 Hz, 1F); ESIMS m/z 330.1 ([M+H]$^+$).

Example 5d 4,5-Dichloro-6-(4-chlorophenyl)picolinonitrile

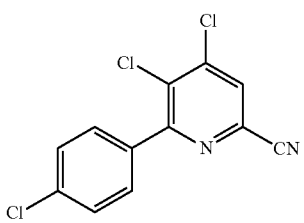 [SMILES: N#Cc1cc(Cl)c(Cl)c(-c2ccc(Cl)cc2)n1]

A 3000 mL round bottom flask was loaded with 4,5,6-trifluoropicolinonitrile (100 g, 0.482 mol), (4-chlorophenyl)boronic acid (106 g, 0.6797 mol), triphenylphosphine (11.4 g, 0.0433 mol) and dipotassium phosphate (K$_2$HPO$_4$; 252 g, 1.4462 mol). Acetonitrile (900 mL) and water (300 mL) were added. The reaction mixture was evacuated/backfilled with nitrogen. Bis(cyanophenyl)palladium(II) dichloride (Pd (PhCN)$_2$Cl$_2$; 9.2 g, 0.0241 mol) was added. The solution was evacuated/backfilled with nitrogen and then stirred at reflux for 5 h. A white solid precipitated upon cooling to room temperature. The reaction mixture was poured into ice water (1000 g) and extracted with EtOAc (3×500 mL). The combined organic layers were successively washed with water (3×500 mL) and brine (100 mL). The extracts were dried over anhydrous Na$_2$SO$_4$, filtered and concentrated under vacuum to give a white solid (83 g, 61%): mp 142.2-144.6° C.; $^1$H NMR (400 MHz, DMSO-d$_6$) δ 8.58 (s, 1H), 7.71 (d, J=8.56 Hz, 2H), 7.61 (d, J=8.56 Hz, 2H); $^{13}$C NMR (75 MHz, DMSO-d$_6$) δ 158.52, 144.49, 135.64, 135.26, 133.20, 131.64, 131.16, 129.84, 128.81, 116.5. Anal. Calcd. for C$_{12}$H$_5$Cl$_3$N$_2$: C, 50.83; H, 1.78; N, 9.88. Found: C, 51.54; H, 1.90; N, 9.19.

Halogenation

Example 6a

Methyl 4-amino-3-chloro-5-fluoro-6-(4-chloro-2-fluoro-3-methoxyphenyl)picolinate

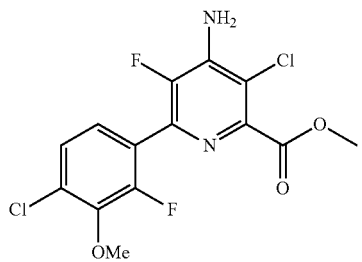 [SMILES: COC(=O)c1nc(-c2ccc(Cl)c(OC)c2F)c(F)c(N)c1Cl]

A mixture of methyl 4-amino-5-fluoro-6-(4-chloro-2-fluoro-3-methoxyphenyl)-picolinate (0.5 g, 1.52 mmol) and 1,3-dichloro-5,5-dimethylimidazolidine-2,4-dione (0.30 g, 1.52 mmol) in acetonitrile (10 mL) was heated to reflux for 1.5 h. Upon cooling to room temperature, the reaction mixture was concentrated under vacuum and then purified by silica gel chromatography (100% hexane to 100% EtOAc gradient) to give a light brown solid (0.53 g, 100%): mp 169-170.5° C.; $^1$H NMR (400 MHz, DMSO-d$_6$) δ 7.48 (d, J=8.4 Hz, 1H), 7.32 (t, J=7.7 Hz, 1H), 7.15 (s, 2H), 3.96 (s, 3H), 3.90 (s, 3H). $^{13}$C NMR (101 MHz, DMSO-d$_6$) δ 164.8 (s), 153.1 (d, J=253 Hz), 146.3 (s), 144.5 (d, J=4 Hz), 143.7 (s), 142.8 (dd, J=227, 14 Hz), 136.4 (d, J=13 Hz), 128.6 (d, J=3 Hz), 125.9 (s), 125.5 (d, J=4 Hz), 122.9 (dd, J=14, 4 Hz), 113.0 (d, J=3 Hz), 61.6 (d, J=4 Hz), 52.7 (s). Anal. Calcd for C$_{14}$H$_{10}$Cl$_2$F$_2$N$_2$O$_3$: C, 46.30; H, 2.78; N, 7.71. Found: C, 46.60; H, 2.68; N, 7.51.

Example 6b

3-Chloro-4,5,6-trifluoropicolinonitrile

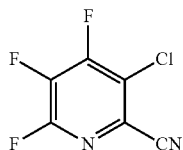

A tubular reactor consisting of a vertical Hastelloy-C-276 tube with a mixing zone (length=48.26 centimeters (cm), ID=1.58 cm, T=290° C.) and a separately heated reaction zone (length=24.13 cm, ID=1.58 cm, T=550° C.) was used. A heated vaporization zone (180° C.), consisting of a 4 foot section of ⅛ inch stainless steel tubing, was attached to the inlet of the tubular reactor. Chlorine gas (5 v % of $Cl_2$ in $N_2$) was directly metered into the mixing zone at 101 mL/min 4,5,6-Trifluoropicolinonitrile (1.013 g, 79% wet solid in hexanes) was dissolved in carbon tetrachloride (39.2 g). This solution was metered through a Gilson pump at 0.1 mL/min rate to the vaporization zone to ensure that the reagents were in the gas phase prior to mixing with chlorine gas in the mixing zone. The condensate from the reactor effluent was collected in a knock-out pot which was installed approximately 7 inches below the reaction zone. The liquid reaction mixture was discharged from the knock-out pot when the run was completed. The sample was analyzed by GC, NMR spectroscopy and GC-MS. GC analysis (Agilent 6890 system, Column: 15 m×0.32 mm J&W DB-5, 0.25 μm; temperature program: 80° C. hold 2 min, ramp 20°/min to 280° C., hold 5 min) showed that the peak area ratio of starting material (4,5,6-trifluoropicolinonitrile) and product (3-chloro-4,5,6-trifluoropicolinonitrile) was approximately 1:1.4. Quantitative $^{13}C$ NMR results showed starting material (4,5,6-trifluoropicolinonitrile) and product (3-chloro-4,5,6-trifluoropicolinonitrile) were major components in the mixture. The mole ratio of starting material and product was approximately 1.0:1.8. GC-MS confirmed the identity of the product as 3-chloro-4,5,6-trifluoropicolinonitrile.

The yield of chlorination product (3-chloro-4,5,6-trifluoropicolinonitrile) was increased significantly when the mixture from the reaction described above was charged to the reactor system one additional time. Use of a two-pass chlorination resulted in an increased conversion with a ratio of product (3-chloro-4,5,6-trifluoropicolinonitrile) to starting material of 2.5:1.0.

Example 6c

Methyl 4-amino-6-(4-chlorophenyl)-5-fluoro-3-iodopicolinate

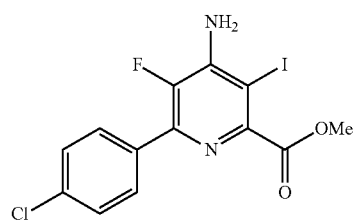 [SMILES: COC(=O)c1nc(-c2ccc(Cl)cc2)c(F)c(N)c1I]

A 250 mL round bottom flask was loaded with methyl 4-amino-6-(4-chlorophenyl)-5-fluoropicolinate (25 g, 0.08906 mol), iodine (18 g, 0.07125 mol), and periodic acid ($H_5IO_6$; 7.3 g, 0.03206 mol). $CH_3OH$ (100 mL) was added. The reaction mixture was stirred at reflux for 16 h. The reaction mixture was concentrated under vacuum and then dissolved in $Et_2O$ (500 mL). The ether solution was washed with 10% sodium thiosulfate (3×100 mL), water (3×100 mL) and then brine. The organic extracts were dried over anhydrous $Na_2SO_4$, filtered and concentrated under vacuum to give an orange solid. Crystallisation from EtOAc-hexane (3:7) gave a pale orange solid (30.5 g, 83%): mp 113.7-115.2° C.; $^1H$ NMR (400 MHz, DMSO-$d_6$) δ 7.84 (d, J=8.4 Hz, 2H), 7.55 (d, J=8.4 Hz, 2H), 6.73 (br s, 2H), 3.87 (s, 3H); $^{13}C$ NMR (100 MHz, DMSO-$d_6$) δ 167.50, 151.48 (d, $J_{F-C}$=5 Hz), 145.95 (d, $J_{F-C}$=13 Hz), 144.05 (d, $J_{F-C}$=257 Hz), 140.75 (d, $J_{F-C}$=9 Hz), 134.56, 133.42 (d, $J_{F-C}$=5 Hz), 130.63 (d, $J_{F-C}$=6 Hz), 129.02, 112.44 (d, $J_{F-C}$=5 Hz), 77.52, 53.05; $^{19}F$ NMR (376.5 MHz, DMSO-$d_6$) δ −140.62; ESIMS m/z 407 ([M]$^+$). Anal. Calcd. For $C_{13}H_9ClFIN_2O_2$: C, 38.40; H, 2.23; N, 6.89. Found: C, 38.40; H, 2.31; N, 6.85.

What is claimed is:

1. A process for the preparation of a 4-amino-5-fluoro-3-halo-6-(substituted)picolinate of the Formula I

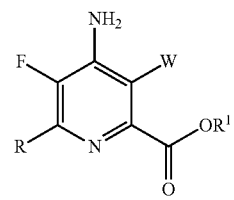

wherein

W represents Cl, Br or I;

R represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; which comprises the following steps:

a) fluorinating 4,5,6-trichloropicolinonitrile (Formula A)

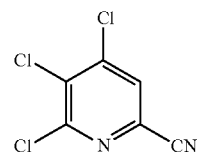

with a source of fluoride ion to produce 4,5,6-trifluoropicolinonitrile (Formula B)

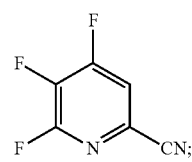

b) aminating 4,5,6-trifluoropicolinonitrile (Formula B) with ammonia to produce 4-amino-5,6-difluoropicolinonitrile (Formula C)

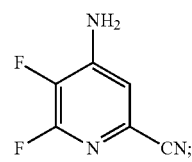

c) hydrolyzing the nitrile substituent and exchanging the fluoro substituent in the 6-position of 4-amino-5,6-difluoropicolinonitrile (Formula C) with an iodo, bromo or chloro substituent by treating with an iodide, bromide or chloride source to produce a 4-amino-5-fluoro-6-halopicolinamide of Formula D

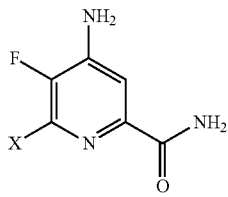

wherein X represents Cl, Br or I;

d) esterifying the 4-amino-5-fluoro-6-halopicolinamide of Formula D with an alcohol (R¹OH) and a Bronsted or Lewis acid to produce a 4-amino-5-fluoro-6-halopicolinate of Formula E

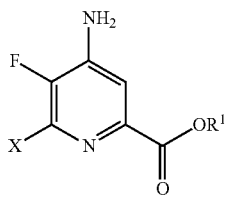

wherein R¹ represents $C_1$-$C_{12}$ alkyl or an unsubstituted or substituted $C_7$-$C_{11}$ arylalkyl;

e) halogenating the 4-amino-5-fluoro-6-halopicolinate of Formula E with a halogen source to produce a 4-amino-5-fluoro-3,6-dihalopicolinate of Formula F

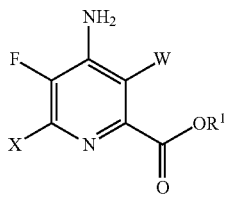

wherein W and X independently represent Cl, Br or I, and R¹ is as previously defined; and f) coupling the 4-amino-5-fluoro-3,6-dihalopicolinate of Formula F with an aryl, alkyl or alkenyl metal compound of the Formula G R-Met                     G wherein R is as previously defined and Met represents Zn-halide, Zn—R, tri-($C_1$-$C_4$ alkyl)tin, copper, or B(OR²)(OR³), where R² and R³ are independent of one another, hydrogen, $C_1$-$C_4$ alkyl, or when taken together form an ethylene or propylene group in the presence of a transition metal catalyst to produce the 4-amino-3-halo-5-fluoro-6-(substituted)picolinate of Formula I.

2. A process for the preparation of a 4-amino-5-fluoro-3-halo-6-(substituted)picolinate of the Formula I

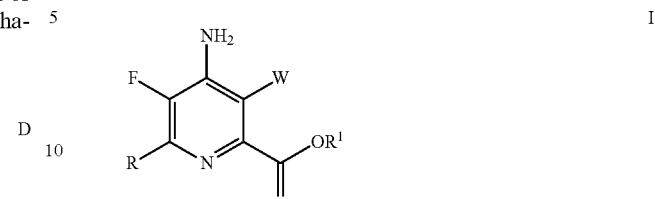

wherein

W represents Cl, Br or I;

R represents $C_1$-$C_4$ alkyl, cyclopropyl, $C_2$-$C_4$ alkenyl, or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and R¹ represents $C_1$-$C_{12}$ alkyl or an unsubstituted or substituted $C_7$-$C_{11}$ arylalkyl; which comprises the following steps:

a) fluorinating 4,5,6-trichloropicolinonitrile (Formula A)

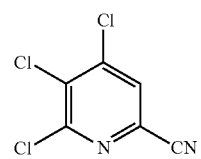

with a source of fluoride ion to produce 4,5,6-trifluoropicolinonitrile (Formula B)

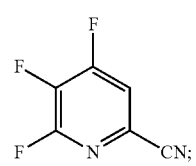

b) aminating 4,5,6-trifluoropicolinonitrile (Formula B) with ammonia to produce 4-amino-5,6-difluoropicolinonitrile (Formula C)

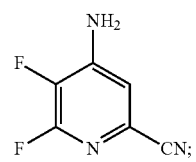

c) hydrolyzing the nitrile substituent and exchanging the fluoro substituent in the 6-position of 4-amino-5,6-difluoropicolinonitrile (Formula C) with an iodo, bromo or chloro substituent by treating with an iodide, bromide or chloride source to produce 4-amino-5-fluoro-6-halopicolinamide of Formula D

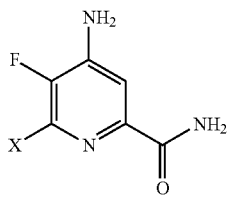

wherein X represents Cl, Br or I;

d) esterifying the 4-amino-5-fluoro-6-halopicolinamide of Formula D with an alcohol (R¹OH) and a Bronsted or Lewis acid to produce a 4-amino-5-fluoro-6-halopicolinate of Formula E

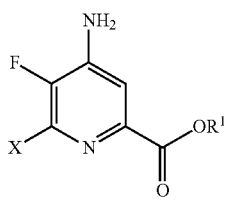

wherein X represents Cl, Br or I, and
R$^1$ represents C$_1$-C$_{12}$ alkyl or an unsubstituted or substituted C$_7$-C$_{11}$ arylalkyl;

e) coupling the 4-amino-5-fluoro-6-halopicolinate of Formula E with an aryl, alkyl or alkenyl metal compound of the Formula G R-Met      G wherein R is as previously defined and Met represents Zn-halide, Zn—R, tri-(C$_1$-C$_4$ alkyl)tin, copper, or B(OR$^2$)(OR$^3$), where R$^2$ and R$^3$ are independent of one another, hydrogen, C$_1$-C$_4$ alkyl, or when taken together form an ethylene or propylene group in the presence of a transition metal catalyst to produce the 4-amino-5-fluoro-6-(substituted)-picolinate of Formula H

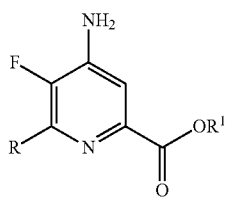

wherein R and R$^1$ are as previously defined; and f) halogenating the 4-amino-5-fluoro-6-(substituted)picolinate of Formula H with a halogen source to produce a 4-amino-5-fluoro-3-halo-6-(substituted)picolinate of Formula I.

3. A process for the preparation of a 4-amino-5-fluoro-3-halo-6-(substituted)picolinate of the Formula I

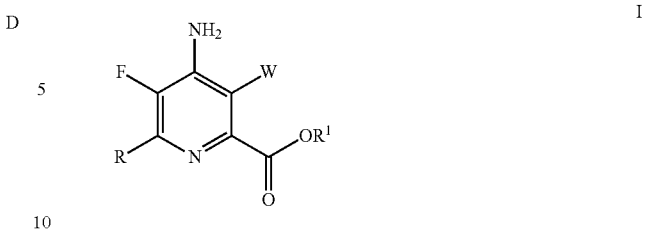

wherein
W represents Cl, Br or I;
R represents C$_1$-C$_4$ alkyl, cyclopropyl, C$_2$-C$_4$ alkenyl or phenyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy; and
R$^1$ represents C$_1$-C$_{12}$ alkyl or an unsubstituted or substituted C$_7$-C$_{11}$ arylalkyl; which comprises the following steps:

a) coupling 4,5,6-trichloropicolinonitrile (Formula A)

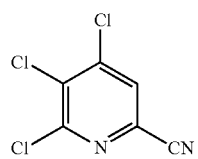

with an aryl, alkyl or alkenyl metal compound of the Formula G

R-Met      G wherein R is as previously defined and Met represents Zn-halide, Zn—R, tri-(C$_1$-C$_4$ alkyl)tin, copper, or B(OR$^2$)(OR$^3$), where R$^2$ and R$^3$ are independent of one another, hydrogen, C$_1$-C$_4$ alkyl, or when taken together form an ethylene or propylene group in the presence of a transition metal catalyst to produce a 4,5-dichloro-6-(substituted)picolinonitrile of Formula J

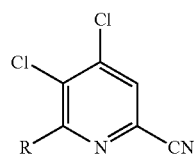

wherein R is as previously defined;

b) fluorinating the 4,5-dichloro-6-(substituted)picolinonitrile of Formula J with a fluoride ion source to produce a 4,5-difluoro-6-(substituted)picolinonitrile of Formula K

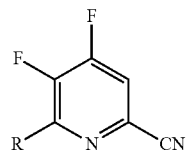

wherein R is as previously defined;

c) aminating the 4,5-difluoro-6-(substituted)picolinonitrile of Formula K with ammonia to produce a 4-amino-5-fluoro-6-(substituted)picolinonitrile of Formula L

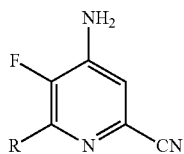

L wherein R is as previously defined;

d) hydrolyzing the 4-amino-5-fluoro-6-(substituted)picolinonitrile of Formula L with an acid to produce the 4-amino-5-fluoro-6-(substituted)picolinamide of Formula M

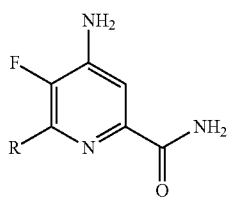

M wherein R is as previously defined;

e) esterifying the 4-amino-5-fluoro-6-(substituted)picolinamide of Formula M with an alcohol ($R^1OH$) and a Bronsted or Lewis acid to produce the 4-amino-5-fluoro-6-(substituted)picolinate of Formula N

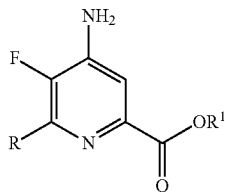

N wherein R and $R^1$ are as previously defined; and f) halogenating the 4-amino-5-fluoro-6-(substituted)picolinate of Formula N with a halogen source to produce the 4-amino-5-fluoro-3-halo-6-(substituted)picolinate of Formula I.

4. A process for the preparation of a 4-amino-5-fluoro-3-halo-6-(substituted)picolinate of the Formula I

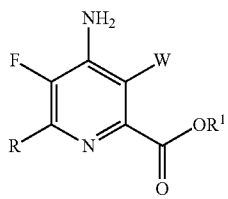

I wherein

W represents Cl, Br or I;

R represents $C_1$-$C_4$ alkyl, cyclopropyl, $C_2$-$C_4$ alkenyl, or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy; and $R^1$ represents $C_1$-$C_{12}$ alkyl or an unsubstituted or substituted $C_7$-$C_{11}$ arylalkyl; which comprises the following steps:

a) fluorinating 4,5,6-trichloropicolinonitrile (Formula A)

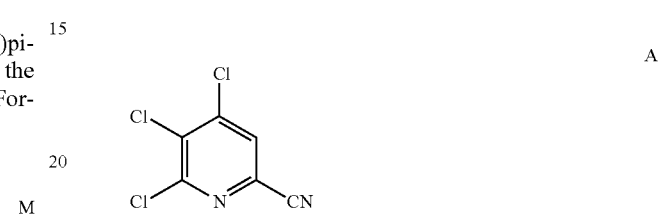

A with a source of fluoride ion to produce 4,5,6-trifluoropicolinonitrile (Formula B)

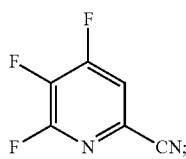

B b) halogenating 4,5,6-trifluoropicolinonitrile (Formula B) with a halogen source to produce a 4,5,6-trifluoro-3-halopicolinonitrile of Formula O

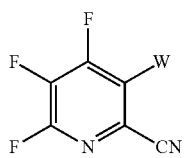

O wherein

W represents Cl, Br or I;

c) aminating the 4,5,6-trifluoro-3-halopicolinonitrile of Formula O with ammonia to produce a 4-amino-5,6-difluoro-3-halopicolinonitrile of Formula P

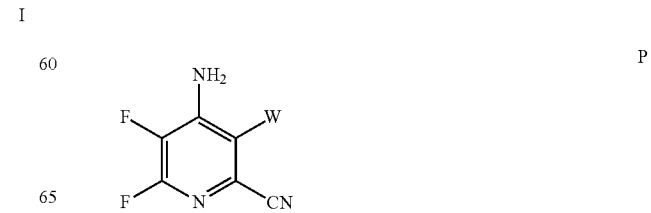

P wherein

W represents Cl, Br or I;

d) hydrolyzing the nitrile substituent and exchanging the fluoro substituent in the 6-position of the 4-amino-5,6-difluoro-3-halopicolinonitrile of Formula P with an iodo, bromo or chloro substituent by treating with an iodide, bromide or chloride source to produce a 4-amino-5-fluoro-3,6-dihalopicolinamide of Formula Q

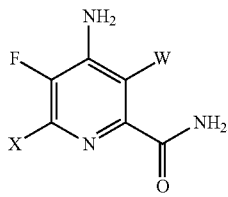

Q wherein W and X independently represent Cl, Br or I;

e) esterifying the 4-amino-5-fluoro-3,6-dihalopicolinamide of Formula Q with an alcohol ($R^1OH$) and a Brønsted or Lewis acid to produce a 4-amino-5-fluoro-3,6-dihalopicolinate of Formula F

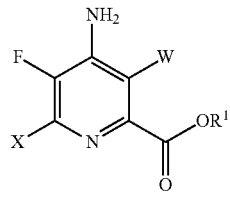

F wherein W and X independently represent Cl, Br or I, and $R^1$ represents $C_1$-$C_{12}$ alkyl or an unsubstituted or substituted $C_7$-$C_{11}$ arylalkyl; and f) coupling the 4-amino-5-fluoro-3,6-dihalopicolinate of Formula F with an aryl, alkyl or alkenyl metal compound of the Formula G R-Met          G wherein R is as previously defined and Met represents Zn-halide, Zn—R, tri-($C_1$-$C_4$ alkyl)tin, copper, or B($OR^2$)($OR^3$), where $R^2$ and $R^3$ are independent of one another, hydrogen, $C_1$-$C_4$ alkyl, or when taken together form an ethylene or propylene group in the presence of a transition metal catalyst to produce a 4-amino-5-fluoro-3-halo-6-(substituted)picolinate of Formula I.

* * * * *